(12) United States Patent
Eriksen et al.

(10) Patent No.: US 9,506,928 B2
(45) Date of Patent: Nov. 29, 2016

(54) METHODS FOR RETRIEVING ANTIGENS USING ALDEHYDE SCAVENGING AGENTS

(71) Applicant: University of Houston System, Houston, TX (US)

(72) Inventors: Jason Eriksen, Houston, TX (US); Craig Vollert, Shenandoah, TX (US); Steven Bark, Houston, TX (US); Wilna Moree, Houston, TX (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 0 days.

(21) Appl. No.: 14/530,142

(22) Filed: Oct. 31, 2014

(65) Prior Publication Data

US 2015/0168417 A1    Jun. 18, 2015

Related U.S. Application Data

(60) Provisional application No. 62/037,905, filed on Aug. 15, 2014, provisional application No. 61/915,271, filed on Dec. 12, 2013.

(51) Int. Cl.
*G01N 33/68* (2006.01)

(52) U.S. Cl.
CPC ................. *G01N 33/6803* (2013.01)

(58) Field of Classification Search
CPC .................. G01N 1/30; G01N 2001/305
See application file for complete search history.

(56) References Cited

U.S. PATENT DOCUMENTS

| | | | |
|---|---|---|---|
| 6,960,450 B2 * | 11/2005 | Namimatsu | 435/40.5 |
| 2009/0202998 A1 | 8/2009 | Schlumpberger et al. | |
| 2012/0295279 A1 | 11/2012 | Kasamatsu | |

FOREIGN PATENT DOCUMENTS

| | | | |
|---|---|---|---|
| EP | 1376096 B1 | | 10/2008 |
| WO | WO-2008095501 A1 | | 8/2008 |
| WO | WO 2011/020612 | * | 2/2011 |
| WO | WO-2013078650 A1 | | 6/2013 |

OTHER PUBLICATIONS

Baschong W. et al. "Control of Autofluorescence of Archival Formaldehyde-fixed, Paraffin-embedded Tissue in Confocal Laser Scanning Microscopy (CLSM)", The Journal of Histochemistry & Cytochemistry, 2001, vol. 49(12), pp. 1565-1571.
Shi Shan-Rong et al. "Protein Extraction from Formalin-fixed, Paraffinembedded Tissue Sections: Quality Evaluation by Mass Spectrometry", Journal of Histochemistry & Cytochemistry, 2006, vol. 54(6), pp. 739-743.

* cited by examiner

*Primary Examiner* — Ralph Gitomer
(74) *Attorney, Agent, or Firm* — Winstead PC

(57) ABSTRACT

Provided herein are methods, compounds, mixtures and formulations of antigen retrieval agent useful in retrieving antigens and improving the detection of amino acids, peptides and proteins or epitopes thereon in a tissue fixed with aldehyde-based cross-linking agents. Contacting the fixed tissue with a solution of the aldehyde scavenging agent causes reactivity with the aldehyde moieties to retrieve antigens and improve detection of the amino acids, peptides and proteins or epitopes. Also provided are kits comprising the antigen retrieval agent and, optionally, components for staining or detecting the proteins or the antigens or epitopes and instructions for using the kit. Further provided is a method for identifying an antigen retrieval agent. A fixed protein is contacted with an agent to be tested and heated in solution therewith. Detection of protein peaks via mass spectrometry indicates the tested agent is an antigen retrieval agent.

12 Claims, 13 Drawing Sheets

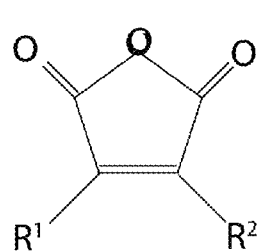
FIG. 1A
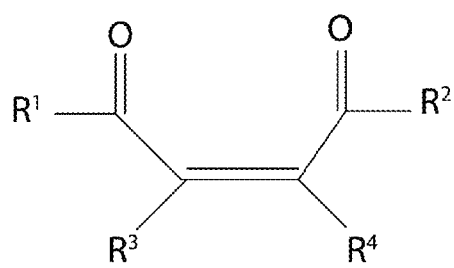
FIG. 1B
FIG. 2A  FIG. 2B
FIG. 2C  FIG. 2D
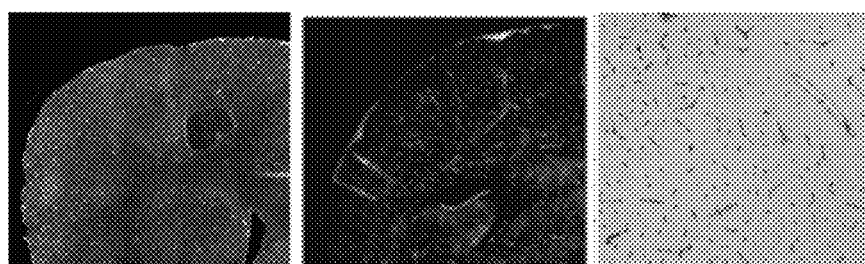
FIG. 3A  FIG. 3B  FIG. 3C

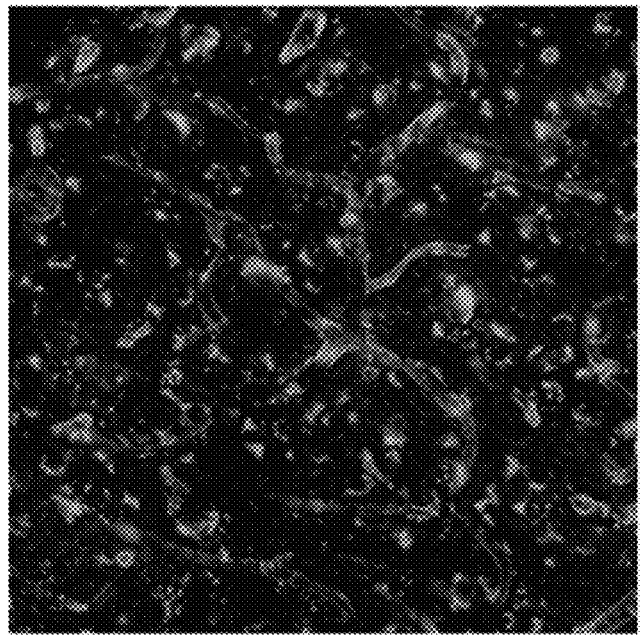
FIG. 7
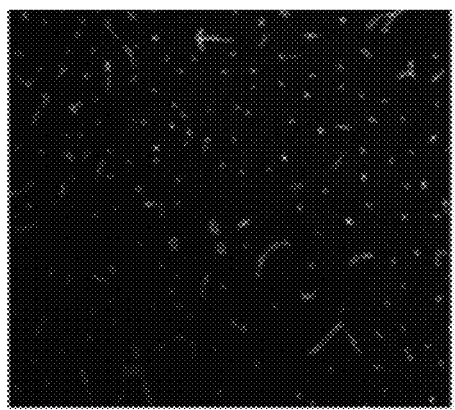 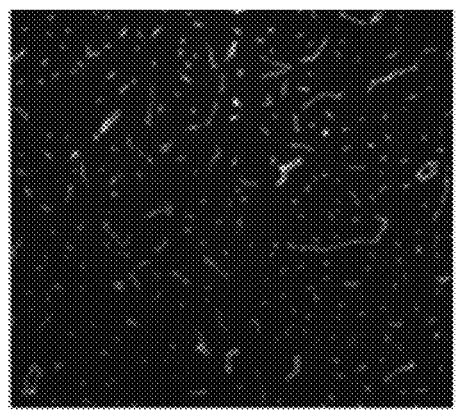
FIG. 8A FIG. 8B

METHODS FOR RETRIEVING ANTIGENS USING ALDEHYDE SCAVENGING AGENTS

CROSS-REFERENCE TO RELATED APPLICATIONS

This nonprovisional application claims benefit of priority under 35 U.S.C. §119(e) of provisional application U.S. Ser. No. 62/037,905, filed Aug. 15, 2014, now abandoned, and provisional application U.S. Ser. No. 61/915,271, filed Dec. 12, 2013, now abandoned, the entirety of both of which is hereby incorporated by reference.

FEDERAL FUNDING LEGEND

This invention was made with government support under Grant Number 1R15AG039008-01 awarded by the National Institutes of Health. The government has certain rights in the invention.

BACKGROUND OF THE INVENTION

Field of the Invention

The present invention relates generally to the fields of histology and the detection of proteins in compositions or tissues that have been preserved using an aldehyde-based cross-linking agent. Specifically, the present invention provides a method of antigen retrieval using aldehyde-scavenging agents to retrieve proteins that have been chemically modified by aldehyde fixatives contained in the compositions or tissues.

Description of the Related Art

Several fixatives are used routinely in a clinical pathology laboratory, like glutaraldehyde, formaldehyde and acetone, or other organic solvents for preservation of biological materials. The vast majority of fixation procedures, however, involve the use of aldehyde-based cross-linking agents, like formaldehyde and glutaraldehyde. The fixative solution is typically an aqueous formaldehyde solution that contains sodium phosphates, configured to provide buffering with minimal pH change following addition of a small amount of strong acid or base to pH 7.2-7.6 and an approximately isotonic solution. The fixation solution adds formaldehyde or glutaraldehyde to various groups on the proteins such as amine groups, phenol groups, thiol groups and hydroxyl groups, initially resulting in a series of reversible modifications, including imines, enamines, hydroxylmethylenes and methylene crosslinks between two amine groups. With prolonged formaldehyde fixation irreversible intermolecular and intramolecular cross-linking can occur within the protein molecules resulting in a dense network that can impair the penetration of paraffin wax or/and the access of antibody molecules. The result is that an antigen of interest may be reversibly or even irreversibly masked or an epitope may be chemically modified or destroyed by reaction with aldehyde-based fixatives.

Despite the broad use and great utility of a variety of immunohistochemical and analytical protein methods in purified proteins, protein extracts, cell or tissue sample, there is great need for further improvements. Such improvements may, for example, relate to a gentler fixation of a cell or tissue sample, to improvements in antigen retrieval or/and reproducibility of results as well as improvements to the use of antibodies to the corresponding antigen or epitope destroyed in standard procedures, like formaldehyde fixation.

Thus, there is a recognized need in the art for improved methods for unmasking proteins and retrieving antigens. Particularly, the prior art is deficient in methods and compounds that are easily formulated to reverse the aldehyde reaction with proteins in fixed tissue by reversal of imine, enamine, and methylenehydroxyl formation on amine groups in the proteins, reversal of methylene crosslinks between amino groups, and other reversible aldehyde modifications on proteins. The present invention fulfills this longstanding need and desire in the art.

SUMMARY OF THE INVENTION

The present invention is directed to a method for retrieving antigens and improving the detection of amino acids, peptides, and proteins in tissues that have been fixed with aldehyde-based cross-linking agents. The method comprises a first step of preparing a solution of an aldehyde scavenging agent. Then a tissue fixed with an aldehyde-based cross-linking agent is contacted with the solution, where a reaction of the aldehyde scavenging agent with the aldehydes comprising the cross-linking agent retrieves the antigens and improves detection of the amino acids, peptides and proteins in the fixed tissue. Since aldehyde and aldehyde adducts exist in a state of reversible equilibrium in the fixed compositions or tissues, aldehyde scavenging agents in the presence of heating and at optimal pH can shift the equilibrium toward releasing aldehyde, resulting in removal of the reversible aldehyde adducts, thereby unmasking the proteins. The present invention is directed to a related method further comprising heating the solution to about 60° C. to about 125° C. to reach a reversible equilibrium between aldehyde and aldehyde adducts. The present invention is directed to another related method further comprising staining the tissue to detect the unmasked protein or an antigen or epitope comprising the same.

The present invention also is directed to formulations of a compound or mixtures of compound in solution useful in the methods as described herein. The compounds can be aldehyde scavenging agents or a mixture thereof. The formulation comprises an aldehyde scavenging agent, an optional nonionic surfactant and a stabilizing agent in a heated solution at a concentration effective to react with the masked proteins.

The present invention is directed further to a kit comprising compounds and/or formulations of an antigen-scavenging agent useful for the antigen retrieval method of the present invention. The kit also comprises a stain, dye, antibody or other components useful to detect the unmasked proteins, peptides, epitopes or antigens and instructions on using the kit.

The present invention is further directed to a method of reducing autofluorescence in tissues caused by heating using the formulations described herein. The present invention is directed further to a method to simultaneously enhance fluorescence intensity after protein unmasking process and remove paraffin from a paraffin embedded sample by applying the optional nonionic surfactant described herein in the solution.

The present invention is directed further still to a method for identifying an antigen retrieval agent. In the method a protein is fixed with an aldehyde-based cross-linking agent to be tested in a aqueous solution and the solution is lyophilized to obtain the fixed protein. The fixed protein is added to a solution containing an agent to be tested as an antigen retrieval agent and the solution containing the compound and fixed protein is heated. The protein is detected by mass spectrometry where the presence of the protein indicates the tested agent is an antigen retrieval agent.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others that will become clear, are attained and can be understood in detail, more particular descriptions of the invention briefly summarized above may be had by reference to certain embodiments thereof that are illustrated in the appended drawings. These drawings form a part of the specification. It is to be noted, however, that the appended drawings illustrate preferred embodiments of the invention and therefore are not to be considered limiting in their scope.

FIGS. 1A-1B depict the basic structure of substituted maleic anhydrides (FIG. 1A) and maleic or (Z)-2-butenedioic acids (FIG. 1B).

FIGS. 2A-2D illustrates antigen retrieval and immunodetection of collagen IV. Paraformaldehyde fixed tissues were subjected to antigen retrieval using TBST (FIG. 2A), low pH (6.0) sodium citrate (FIG. 2B), pepsin pretreatment (FIG. 2C), and 0.05% maleic anhydride pretreatment (FIG. 2D).

FIGS. 3A-3C illustrate antigen retrieval in fixed tissue via visualization via immunohistochemical methods. Paraformaldehyde fixed cryostat sectioned tissues are visualized using immunofluorescence (FIG. 3A), formaldehyde fixed paraffin embedded tissue is visualized using immunofluorescence (FIG. 3B) and formaldehyde fixed paraffin embedded tissue is visualized using a DAB chromagen by immunohistochemistry (FIG. 3C).

FIG. 7 is a microscope image showing collagen IV staining of blood vessels in paraformaldehyde fixed adult human brain tissue after antigen retrieval.

FIGS. 8A-8B show microscope images showing enhancement of fluorescence after antigen retrieval process by the addition of nonionic surfactant Triton X-100 (FIG. 8B) compared to 0.05% ascorbic acid alone (FIG. 8A).

DETAILED DESCRIPTION OF THE INVENTION

Figures 4A, 4B:
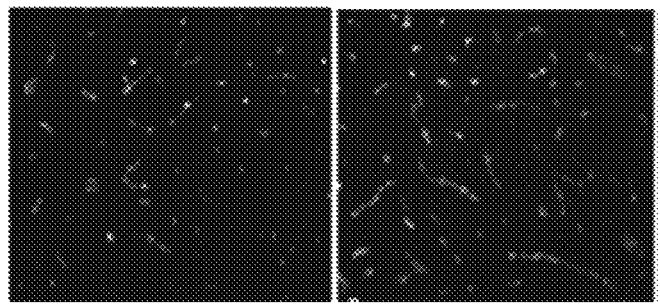
FIGS. 4A-4E compare antigen retrieval in fixed vascular tissue using maleic acid (FIG. 4A), maleic anhydride (FIG. 4B), 2,3-dimethyl maleic anhydride (FIG. 4C), fumaric acid (FIG. 4D), and succinic acid (FIG. 4E).

As used herein, the following terms and phrases shall have the meanings set forth below. Unless defined otherwise, all technical and scientific terms used herein have the same meaning as commonly understood to one of ordinary skill in the art.

As used herein, the term, "a" or "an" may mean one or more. As used herein in the claim(s), when used in conjunction with the word "comprising", the words "a" or "an" may mean one or more than one. As used herein "another" or "other" may mean at least a second or more of the same or different claim element or components thereof. The terms "comprise" and "comprising" are used in the inclusive, open sense, meaning that additional elements may be included.

As used herein, the term "or" in the claims refers to "and/or" unless explicitly indicated to refer to alternatives only or the alternatives are mutually exclusive, although the disclosure supports a definition that refers to only alternatives and "and/or".

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the term "unmasking" refers to retrieving antigens and/or improving the detection of amino acids, peptides, and proteins in a fixed tissue.

In one embodiment of the present invention, there is provided a method for retrieving antigens and improving the detection of amino acids, peptides, and proteins in a fixed tissue, comprising the steps of preparing a solution of an aldehyde scavenging agent; and contacting a tissue fixed with an aldehyde-based cross-linking agent with the solution; wherein a reaction of the aldehyde scavenging agent with the aldehydes comprising the cross-linking agent retrieves the antigens and improves detection of the amino acids, peptides and proteins in the fixed tissue.

Further to this embodiment the method comprises heating the solution to about 60° C. to about 125° C. for a duration of about 30 minutes to about 48 hours, wherein at this temperature there is a reversible equilibrium between aldehyde and aldehyde adducts. In this further embodiment the solution of these compounds reduces autofluorecence in heated tissues. Further still to this embodiment the method comprises staining the tissue to detect the retrieved protein or an antigen or epitope comprising the protein or antigen.

In all embodiments, the concentration of the solution of an aldehyde scavenging agent is about 0.05% to about 30%. Also, the pH of the solution is maintained with in a range specific for the aldehyde scavenging agents. In addition in all embodiments, a representative aldehyde-based cross-linking agent may be formaldehyde or glutaraldehyde. The aldehyde scavenging agent are listed in, but not limited to, Table 1. Particularly, the compound may be aminoethanol, N-Methylaminoethanol, 2-(hydroymethyl)piperidine, 2-(hydroxymethyl)pyrrolidine, N-benzylaminoethanol, Amino (bis ethanol), 2-amino-2-methyl-1,3-propanediol; serine, threonine, chitosan, tris(hydroxymethyl)aminomethane, arginine, lysine, glycine, histidine, 5-hydroxytryptophane, carnosine, guanidine, morpholine, 2-hydroxymethylpiperidine, ammonia, ammoniumcarbonate, hydroxylamine, O-alkylated hydroxylamine, N-alkylated hydroxylamine, O,N-alkylated hydroxylamine, hydroxymethylamine, methoxyamine, dibutylamine, triethylenetetramine, benzylamine, thiabendazole, benzotriazol, triazole, indoline, benzoguanamine, 3,4-diaminobenzoic acid, methyl 4-aminobenzoate, aniline; 1-amino-2-indole; a polyoxyalkylene amine; a polyamidoamine, anthranilic acid, methyl anthranilate, anthranilamide; o-phenylenediamine; 4-aminobenzoic acid; 3,4-diaminobenzoic acid; hydrazine, N-methylhydrazine, N-phenylhydrazine, methylhydrazide, 2,4-dinitrophenylhydrazide, urea, allantoin, imidazolidone, phenobarbital, glycoluril, biuret, cysteamine, cysteine, glutathione, sodiumbisulfite, o-mercaptobenzamide, malonamide, oxamide, acetoacetamide, oxamide, pyroglutamic acid, succinamide, ethylenediamine-N,N'-bisacetoacetamide, N-(2-ethylhexyl)acetoacetamide, N-(3-phenylpropyl)acetoacetamide, a polyamide; a polyesteramide, sorbitol, hexane diol, glucose, cellulose, hydroxycitronellol, dimedone, ascorbic acid, pentane dione, 2-butanone, cyclohexanone, 2,2-dimethyl-I,3-dioxan-4,6-dione, 2-pentanone, 5,5-dimethyl-1,3-cyclohexanedione, dehydroacetic acid, 1,3-dihydroxyacetone dimer, methyl gallate, ethyl gallate, propyl gallate, pyrogallol, salicylamide; salicylanilide; 4,5-dihydroxy-2,7-naphthalenedisulfonic acid, citraconic acid, maleic anhydride, 2,3-dimethylmaleic anhydride, 1(E)-2-Butenedioic acid dimethyl ester, 2-sulfanylbut-2-enedioic acid, but-2-enedioic acid, (E)-3-nitroprop-2-enoate, (E)-2,3-dideuteriobut-2-enedioic acid, (Z)-2-methoxybut-2-enedioic acid, (Z)-2-hydroperoxybut-2-enedioic acid, 2-methoxybut-2-enedioic acid, (Z)-2-fluorobut-2-enedioate, 4-oxopent-2-enoic acid, (E)-2,3-dichlorobut-2-enedioic acid, Dichloromaleic acid, (Z)-2-iodobut-2-enedioic acid, (E)-2,3-dideuteriobut-2-enedioic acid, (Z)-2-hydroxy-3-methylbut-2-enedioic acid, 2,3-dideuteriobut-2-enedioic acid, (E)-3-nitrobut-2-enoic acid, but-2-enedioate, (E)-4-chloro-4-oxobut-2-enoate, (E)-2,3-difluorobut-2-enedioate, (E)-4-hydroxy-4-oxobut-2-enoate, hydrogen fumarate, (Z)-2-sulfanylbut-2-enedioic acid, 2,3-Difluorofumaric acid, (E)-4-hydroxy-2-methyl-4-oxobut-2-enoate, mono fluorofumarate, fluorofumaric acid, (Z)-2-chlorobut-2-enedioic acid, 2-hydroperoxybut-2-enedioic acid, Peroxymaleic acid, 2-chloro-3-methylbut-2-enedioic acid, 2-chloro-3-methylbut-2-enedioic acid, 2-Butenedioicacid, [(E)-3-carboxy-1-hydroxyprop-2-enylidene]oxidanium, (E)-2-methylbut-2-enedioate, 2-methylfumarate, Citraconic acid, 2,3-dichloromaleic acid, 3,4-Dichloro-5-hydroxyfuran-2 (5H)-one, 3-chlorocarbonylacrylic acid ethyl ester, (E)-Ethyl 4-oxopent-2-enoate, [(Z)-3-carboxyprop-2-enoyl]oxidanium, (Z)-but-2-enedioic acid, dimethyl maleate, dimethyl fumarate; activated carbon, alumina; silica; amine functionalized silica; talc; zeolites; or a poly functional organic species containing both a primary, or secondary amine group and a carboxylic acid, phenolic, amide, hydroxyl, urea, ester or thiol group, at least one of which reacts with aldehyde;

cyclodextrins; or combinations of any of these compounds.

In all embodiments, the solution of an aldehyde scavenging agent further may contain about 0.1% to about 5% of a nonionic surfactant which removes paraffin from a paraffin embedded sample and enhances fluorescence intensity after the antigen is retrieved. Representative examples of nonionic surfactants include but are not limited to Cetomacrogol 1000, Cetostearyl alcohol, Cetyl alcohol, cocamide diethanolamine, cocamide monoethanolamine, Decyl glucoside, IGEPAL CA-630, Isoceteth-20, Lauryl glucoside, NP-40, Nonidet P-40, Nonoxynol-9, nonoxynols, Monolaurin, Octaethylene glycol monododecyl ether, Oleyl alcohol, Poloxamers, Poloxamer 407, Polyglycerol polyricinoleate, Polysorbates, Sorbitan monostearate, Sorbitan tristearate; Stearyl alcohol; Triton X-10; Tween 80.; octyl-, decyl, dodecyl-glucopyranoside, -maltoside, and deoxycholic acid.

In these embodiments, the solution further may contain a stabilizing agent.

Representative examples of stabilizing agents include but are not limited to a preservative, an antifungal agent, an antibacterial agent, a dye, a pigment, anionic detergents, metal salts, antioxidants or a combination thereof. In one preferred embodiment, the stabilizing agent is glutathione in a concentration range of about 2 mM to about 400 mM.

In another embodiment of the present invention, there is provided a formulation comprising one compound or a mixture of compounds in solution, an optional nonionic surfactant and a stabilizing agent described supra in a heated solution at a concentration effective to react with the masked proteins, within a pH range particular for the compounds to be effective aldehyde scavenging agents, and a temperature range where there is an equilibrium between aldehyde and aldehyde adducts or that enhances the rate of attaining equilibrium between aldehyde and aldehyde adducts. Particularly, the formulation may comprise the compound or mixture of the compounds at the concentration of about 0.05% to about 30%, and may further contain an optional nonionic surfactant thereof at a concentration of about 0.1 to a bout 5% and a stabilizing agent in a solution comprising water. Examples of the stabilizing agent are, but are not limited to, a preservative, an antifungal agent, an antibacterial agent, a dye, a pigment, anionic detergents, metal salts, antioxidants or a combination thereof.

In yet another embodiment of the present invention there is provided a kit for retrieve a protein of interest in a fixed tissue, comprising an aldehyde scavenging agents as described supra, an optional nonionic surfactant as described supra, a stabilizing agent as described supra, a stain, dye or antibody and instructions on using the kit.

In yet another embodiment of the present invention, there is provided a method for identifying an antigen retrieval agent, comprising the steps of fixing a protein with aldehyde-based cross-linking agent to be tested in an aqueous solution; lyophilizing the solution by to obtain fixed protein; adding the fixed protein to a solution containing an agent to be tested as an antigen retrieval agent; heating the solution containing the agent to be tested and the fixed protein; detecting the protein with mass spectrometry; wherein the presence of peaks for the protein indicates the tested agent is an antigen retrieval agent. In this embodiment, the aldehyde-based cross-linking agent comprises about 4% formaldehyde in water. The solution is heated up to a temperature range from about 60° C. to about 125° C. from about 30 minutes to 48 hours.

Provided herein are methods, compounds and kits useful for unmasking and detecting proteins masked in tissues fixed with aldehyde-based cross-linking agents. Particularly, any compounds that function as aldehyde scavenging agents in a specific pH range are useful for antigen retrieval. The compounds display reactivity towards released aldehyde, formed by hydrolysis of fixative adducts to proteins in tissue formed during aldehyde fixation, shifting the equilibrium between aldehyde and aldehyde adducts toward (form) aldehyde in the fixed tissue. A representative list of applicable compounds is shown in Table 1.

TABLE 1

| Number | Compound |
|---|---|
| 1 | (E)-2-Butenedioic acid dimethyl ester |
| 2 | 2-sulfanylbut-2-enedioic acid |
| 3 | but-2-enedioic acid |
| 4 | (E)-3-nitroprop-2-enoate |
| 5 | (E)-2,3-dideuteriobut-2-enedioic acid |
| 6 | (Z)-2-methoxybut-2-enedioic acid |
| 7 | (Z)-2-hydroperoxybut-2-enedioic acid |
| 8 | 2-methoxybut-2-enedioic acid |
| 9 | (Z)-2-fluorobut-2-enedioate |
| 10 | 4-oxopent-2-enoic acid |
| 11 | (E)-2,3-dichlorobut-2-enedioic acid |
| 12 | Dichloromaleic acid |
| 13 | (Z)-2-iodobut-2-enedioic acid |
| 14 | (E)-2,3-dideuteriobut-2-enedioic acid |
| 15 | (Z)-2-hydroxy-3-methylbut-2-enedioic acid |
| 16 | 2,3-dideuteriobut-2-enedioic acid |
| 17 | (E)-3-nitrobut-2-enoic acid |
| 18 | but-2-enedioate |
| 19 | (E)-4-chloro-4-oxobut-2-enoate |
| 20 | (E)-2,3-difluorobut-2-enedioate |
| 21 | (E)-4-hydroxy-4-oxobut-2-enoate |
| 22 | Hydrogen fumarate |
| 23 | (Z)-2-sulfanylbut-2-enedioic acid |
| 24 | 2,3-Difluorofumaric acid |
| 25 | (E)-4-hydroxy-2-methyl-4-oxobut-2-enoate |
| 26 | Monofluorofumarate |
| 27 | Fluorofumaric acid |
| 28 | (Z)-2-chlorobut-2-enedioic acid |
| 29 | 2-hydroperoxybut-2-enedioic acid |
| 30 | Peroxymaleic acid |
| 31 | 2-chloro-3-methylbut-2-enedioic acid |
| 32 | 2-chloro-3-methylbut-2-enedioic acid |
| 33 | 2-Butenedioicacid |
| 34 | [(E)-3-carboxy-1-hydroxyprop-2-enylidene] oxidanium |
| 35 | (E)-2-methylbut-2-enedioate |
| 36 | 2-methylfumarate |
| 37 | Citraconic acid |
| 38 | 2,3-Dichloromaleic acid |
| 39 | 3,4-Dichloro-5-hydroxyfuran-2(5H)-one |
| 40 | 3-Chlorocarbonylacrylic acid ethyl ester |
| 41 | (E)-Ethyl 4-oxopent-2-enoate |
| 42 | O-methylhydroxylamine |
| 43 | [(Z)-3-carboxyprop-2-enoyl]oxidanium |
| 44 | (Z)-but-2-enedioic acid |
| 45 | Dimethyl maleate |
| 46 | Dimethyl fumarate |
| 47 | aminoethanol |
| 48 | N-Methylaminoethanol |
| 49 | 2-(hydroymethyl)piperidine |
| 50 | 2-(hydroxymethyl)pyrrolidine |
| 51 | N-benzylaminoethanol |
| 52 | Amino(bis ethanol), |
| 53 | 2-amino-2-methyl-1,3-propanediol |
| 54 | serine |
| 55 | threonine |
| 56 | chitosan |
| 57 | tris(hydroxymethyl)aminomethane |
| 58 | amino acids and derivatives including, arginine, lysine, glycine, histidine, 5-hydroxytryptophane, carnosine, |
| 59 | other amine and aniline containing compounds including guanidine, morpholine, 2-hydroxymethylpiperidine, ammonia, ammoniumcarbonate, hydroxylamine, O-alkylated hydroxylamine, N-alkylated hydroxylamine, O,N-alkylated hydroxylamine, hydroxymethylamine, methoxyamine, dibutylamine, triethylenetetramine, benzylamine, thiabendazole, benzotriazol, triazole, indoline, benzoguanamine, 3,4-diaminobenzoic acid, methyl 4-aminobenzoate, aniline |
| 60 | 1-amino-2-indole |
| 61 | a polyoxyalkylene amine |
| 62 | a polyamidoamine, anthranilic acid, methyl anthranilate, anthranilamide |
| 63 | o-phenylenediamine |
| 64 | 4-aminobenzoic acid |

TABLE 1-continued

| Number | Compound |
|---|---|
| 65 | 3,4-diaminobenzoic acid |
| 66 | hydrazine and hydrazide derivatives including, hydrazine, N-methylhydrazine, N-phenylhydrazine, methylhydrazide, 2,4-di-nitrophenylhydrazide |
| 67 | urea derivatives including urea, allantoin, imidazolidone, phenobarbital, glycoluril, biuret, |
| 68 | thiol derivatives including cysteamine, cysteine, glutathione, sodiumbisulfite, o-mercaptobenzamide, |
| 69 | amide derivatives including malonamide, oxamide, acetoacetamide, oxamide, pyroglutamic acid, succinamide, ethylenediamine-N,N'-bisacetoacetamide, N-(2-ethylhexyl)acetoacetamide, N-(3-phenylpropyl)acetoacetamide, a polyamide |
| 70 | a polyesteramide |
| 71 | hydroxyl compounds including sorbitol, hexane diol, glucose, cellulose, hydroxycitronellol |
| 72 | keto derivatives including, dimedone, ascorbic acid, pentane dione, 2-butanone, cyclohexanone, 2,2-dimethyl-1,3-dioxan-4,6-dione, 2-pentanone, 5,5-dimethyl-1,3-cyclohexanedione, dehydroacetic acid, 1,3-dihydroxyacetone dimer |
| 73 | phenolic derivatives including methyl gallate, ethyl gallate, propyl gallate, pyrogallol, salicylamide; salicylanilide; 4,5-dihydroxy-2,7-naphthalenedisulfonic acid, |
| 74 | solid phase materials including activated carbon, alumina; silica; amine functionalized silica |
| 75 | talc |
| 76 | zeolites |
| 77 | poly functional organic species containing both a primary, or secondary amine group and a carboxylic acid, hydroxyl, urea, phenolic, amide, ester or thiol group, at least one of which is capable of reacting with aldehyde |
| 78 | cyclodextrin compounds |

As described in the Examples, the method provided herein utilizes compounds formulated in solution, for example in water, at a concentration of about 0.05% to 30%. Heating of the fixed tissue at optimized pH range will liberate aldehydes which can react with the compounds in solution to unmask proteins of interest. One compound or a mixture of compounds may be utilized in the formulation. Subsequent to unmasking, one or more proteins of interest may be detected by a method selected from staining, immunohistochemical or histopathological or other procedures known in the art based on the one or more proteins of interest.

In fixed tissues, these compounds allow for robust detection of proteins such as vascular proteins and preserves tissue morphology. Moreover, these compounds preserve the detection of DNA in situ using conventional nucleic acid binding dyes such as DAPI, enabling multicolor imaging in histopathological procedures.

Thus, also provided are novel compounds and formulations thereof useful in the methods described herein. The formulations may contain an optional nonionic surfactant that can simultaneously enhance the fluorescence intensity after a protein unmasking process and remove paraffin from a paraffin embedded sample, eliminating a separate dewaxing step. Nonionic surfactants are include but are not limited to Cetomacrogol 1000, Cetostearyl alcohol, Cetyl alcohol, cocamide diethanolamine, cocamide monoethanolamine, Decyl glucoside, IGEPAL CA-630, Isoceteth-20, Lauryl glucoside, NP-40, Nonidet P-40, Nonoxynol-9, nonoxynols, Monolaurin, Octaethylene glycol monododecyl ether, Oleyl alcohol, Poloxamers, Poloxamer 407, Polyglycerol polyricinoleate, Polysorbates, Sorbitan monostearate, Sorbitan tristearate; Stearyl alcohol; Triton X-10; Tween 80; and octyl-, decyl, dodecyl-glucopyranoside, -maltoside, and deoxycholic acid.

Further provided herein are kits useful for unmasking proteins in fixed tissue.

These kit may comprise one or more novel compounds or the formulations thereof described herein in combination with an antibody or other agent used for detection. Such kits enable the one-step antigen retrieval method for detection of a wide variety of proteins. With the kits, a user may take fixed tissue that has been stored in a variety of conditions, such as paraformaldehyde, formalin, ethanol, or in paraffin blocks, subject these fixed tissues to brief chemical treatments, and then analyze proteins using quantitative techniques such as western blotting and ELISA. These applications enable one of ordinary skill in the art to use vast quantities of archival tissue that currently cannot be used for quantitative protein analysis because of loss of sensitivity due to fixation.

The following examples are given for the purpose of illustrating various embodiments of the invention and are not meant to limit the present invention in any fashion.

EXAMPLE 1

Compounds

Representative aldehyde scavenging agents effective to react with aldehyde within a particular pH range include but are not limited to amino ethanol derivatives including, aminoethanol, N-Methylaminoethanol, 2-(hydroymethyl)piperidine, 2-(hydroxymethyl)pyrrolidine, N-benzylaminoethanol, Amino(bis ethanol), 2-amino-2-methyl-1,3-propanediol; serine, threonine, chitosan, tris(hydroxymethyl) aminomethane, amino acids and derivatives including, arginine, lysine, glycine, histidine, 5-hydroxytryptophane, carnosine, other amine and aniline containing compounds including guanidine, morpholine, 2-hydroxymethylpiperidine, ammonia, ammoniumcarbonate, hydroxylamine, O-alkylated hydroxylamine, N-alkylated hydroxylamine, O,N-alkylated hydroxylamine, hydroxymethylamine, methoxyamine, dibutylamine, triethylenetetramine, benzylamine, thiabendazole, benzotriazol, triazole, indoline, benzoguanamine, 3,4-diaminobenzoic acid, methyl 4-aminobenzoate, aniline; 1-amino-2-indole; a polyoxyalkylene amine; a polyamidoamine, anthranilic acid, methyl anthranilate, anthranilamide; o-phenylenediamine; 4-aminobenzoic acid; 3,4-diaminobenzoic acid; hydrazine and hydrazide derivatives including, hydrazine, N-methylhydrazine, N-phenylhydrazine, methylhydrazide, 2,4-di-nitrophenylhydrazide, urea derivatives including urea, allantoin, imidazolidone, phenobarbital, glycoluril, biuret, thiol derivatives including cysteamine, cysteine, glutathione, sodiumbisulfite, o-mercaptobenzamide, amide derivatives including malonamide, oxamide, acetoacetamide, oxamide, pyroglutamic acid, succinamide, ethylenediamine-N,N'-bisacetoacetamide, N-(2-ethylhexyl)acetoacetamide, N-(3-phenylpropyl)acetoacetamide, a polyamide; a polyesteramide, hydroxyl compounds including sorbitol, hexane diol, glucose, cellulose, hydroxycitronellol, keto derivatives including, dimedone, ascorbic acid, pentane dione, 2-butanone, cyclohexanone, 2,2-dimethyl-I,3-dioxan-4,6-dione, 2-pentanone, 5,5-dimethyl-I,3-cyclohexanedione, dehydroacetic acid, 1,3-dihydroxyacetone dimer, phenolic derivatives including methyl gallate, ethyl gallate, propyl gallate, pyrogallol, salicylamide; salicylanilide; 4,5-dihydroxy-2,7-naphthalenedisulfonic acid, acid and ester derivatives including maleic acid, citraconic acid, maleic anhydride, 2,3-dimethylmaleic anhydride, 1 (E)-2-Butenedioic acid dimethyl ester, 2-sulfanylbut-2-enedioic acid, but-2-enedioic acid, (E)-3-nitroprop-2-enoate, (E)-2,3-dideuteriobut-2-enedioic acid, (Z)-2-methoxybut-2-enedioic acid, (Z)-2-hydroperoxybut-2-enedioic acid, 2-methoxybut-2-enedioic acid, (Z)-2-fluorobut-2-enedioate, 4-oxopent-2-enoic acid, (E)-2,3-dichlorobut-2-enedioic acid, Dichloromaleic acid, (Z)-2-iodobut-2-enedioic acid, (E)-2,3-dideuteriobut-2-enedioic acid, (Z)-2-hydroxy-3-methylbut-2-enedioic acid, 2,3-dideuteriobut-2-enedioic acid, (E)-3-nitrobut-2-enoic acid, but-2-enedioate, (E)-4-chloro-4-oxobut-2-enoate, (E)-2,3-difluorobut-2-enedioate, (E)-4-hydroxy-4-oxobut-2-enoate, hydrogen fumarate, (Z)-2-sulfanylbut-2-enedioic acid, 2,3-Difluorofumaric acid, (E)-4-hydroxy-2-methyl-4-oxobut-2-enoate, monofluorofumarate, fluorofumaric acid, (Z)-2-chlorobut-2-enedioic acid, 2-hydroperoxybut-2-enedioic acid, Peroxymaleic acid, 2-chloro-3-methylbut-2-enedioic acid, 2-chloro-3-methylbut-2-enedioic acid, 2-Butenedioicacid, [(E)-3-carboxy-1-hydroxyprop-2-enylidene]oxidanium, (E)-2-methylbut-2-enedioate, 2-methylfumarate, Citraconic acid, 2,3-dichloromaleic acid, 3,4-Dichloro-5-hydroxyfuran-2(5H)-one, 3-chlorocarbonylacrylic acid ethyl ester, (E)-Ethyl 4-oxopent-2-enoate, [(Z)-3-carboxyprop-2-enoyl] oxidanium, (Z)-but-2-enedioic acid, dimethyl maleate, dimethyl fumarate solid phase materials including activated carbon, alumina; silica; amine functionalized silica; talc; zeolites; or a poly functional organic species containing both a primary, or secondary group and a carboxylic acid, hydroxyl, urea, phenolic, amide, ester or thiol group, at least one of which is capable of reacting with aldehyde; cyclodextrins; or combinations of any of these compounds.

EXAMPLE 2

Antigen Retrieval in Formaldehyde Fixed Tissue: General Method

Small amounts of one or a mixture of compounds, for example, from Table 1 are added to water, in a 0.05% concentration. The solution is heated to about 70° C. to about 95° C. for about 30 minutes. The ensuing chemical reaction enables the unmasking or retrieval of the chemical epitopes. The formaldehyde-fixed tissue is placed into the heated solution for about 30 minutes and then washed. The tissues can then be stained to detect the protein of interest. Superior antigen retrieval and immunodetection of collagen IV, a vascular protein, in paraformaldehyde fixed tissues was demonstrated using maleic anhydride (FIGS. 2A-2D).

EXAMPLE 3

Antigen Retrieval is Cross Compatible with Different Immunohistochemical Methods The method of antigen retrieval is compatible and enhances visualization of proteins in multiple forms of processed tissues. Micrographs illustrate an enhanced visualization in paraformaldehyde fixed cryostat sectioned tissues visualized using immunofluorescence, and formaldehyde fixed paraffin embedded tissue visualized using a DAB chromagen by immunohistochemistry (FIGS. 3A-3D).

EXAMPLE 4

Figures 4C, 4D, 4E:
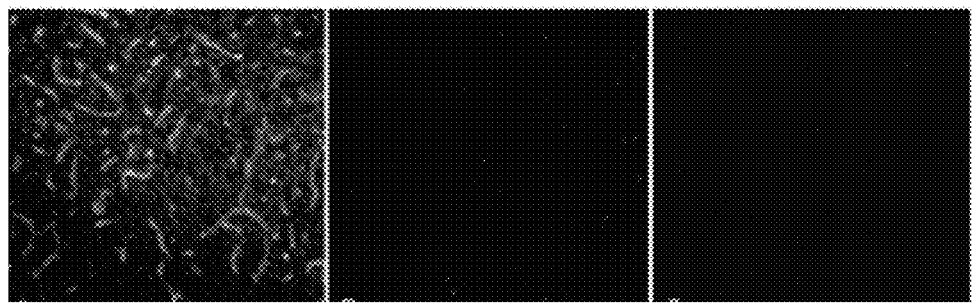
Figures 5A, 5B:
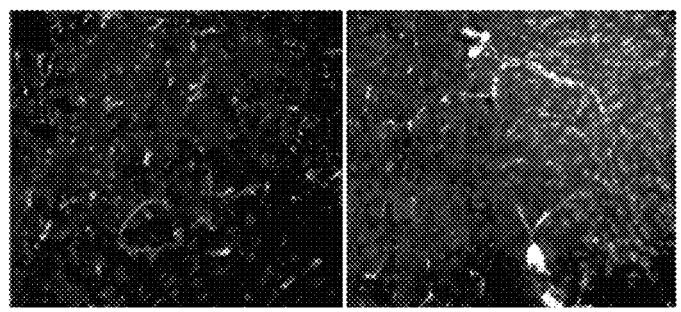
FIGS. 5A-5D demonstrate retrieval of endothelin-1 (FIG. 5A), VEGF (FIG. 5B), von Willebrand (FIG. 5C), and both alpha-smooth muscle actin and collagen IV (FIG. 5D).
Figures 5C, 5D:
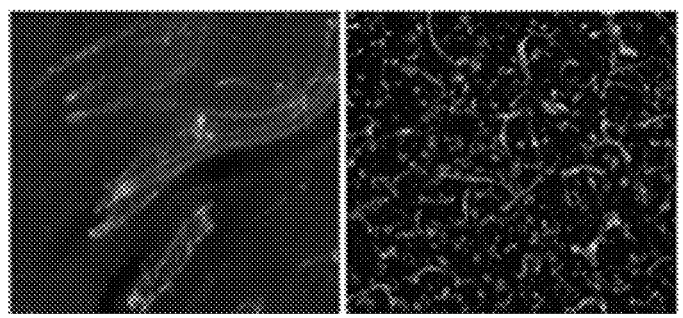

Maleic Acid, Maleic Anhydride and 2,3 Dimethylmaleic Anhydride as Antigen Retrieval Agents Succinic anhydride was used as a test. Paraformaldehyde fixed tissue samples are heated in solutions of compounds prepared as described in Example 1 and the blood vessels in the tissue are visualized. In maleic acid (FIG. 4A), maleic anhydride (FIG. 4B), and 2,3 dimethylmaleic anhydride related tissue demonstrates successful antigen retrieval with visualization of the blood vessels (FIG. 4C). FIG. 4D shows that the cis-configuration at the alpha,beta double bond of these compounds yields a substantially higher activity than treatment with fumaric acid, which contains a trans-configuration demonstrates a significant reduction in activity. In distinct contrast, FIG. 4E demonstrates no vasculature is visible in the succinic anhydride treated tissue. This demonstrates that the cis-configuration is superior for antigen retrieval.

EXAMPLE 5

Vascular Antigen Retrieval in Adult Mouse Brain Tissue with Maleic Anhydride 12-month-old C 57 black 6J mice and six month were housed under controlled environment conditions on a conventional 12 hour light dark cycle. Following sacrifice, brains were post-fixed in 4% percent paraformaldehyde for 72 hours at 4° C. and then transferred to a 70% ethanol solution where they were stored at 4° C. Tissue was paraffin-processed using convention dehydration and embedding, and then sectioned at 5 μm intervals. Cryosectioned tissue was embedded in Optimal cutting temperature compound (Tissue-Tek) and then frozen at −80° C.; 50 μm sections were cut on a cryostat (Leica). In studies where different processing studies were conducted, adjacent sections were used for comparison.

For sections incubated in carbonic anhydride solution, 50 μm sections were incubated in PBS containing 0.2% Triton X-100 three times for ten minutes each, and then slices were immersed for 45 minutes in a 0.05% maleic anhydride (Sigma Aldrich) solution in distilled water, prewarmed to 95° C. Sections were cooled to room temperature and then washed in four changes of PBS for 15 min, prior to processing through immunohistochemistry.

Treatment of formaldehyde fixed tissues with maleic anhydride was used to unmask a broad variety of vascularassociated antigens normally masked by aldehyde-based fixation. Endothelin-1, VEGF, von Willebrand and, using double labeling, alpha-smooth muscle actin and collagen IV (FIGS. 5A-5D), were unmasked using antibodies that have been reported to work in tissue.

EXAMPLE 6

Antigen Retrieval from Tissue Homogenates from Formaldehyde Fixed Brain Tissue

Figure 6A:
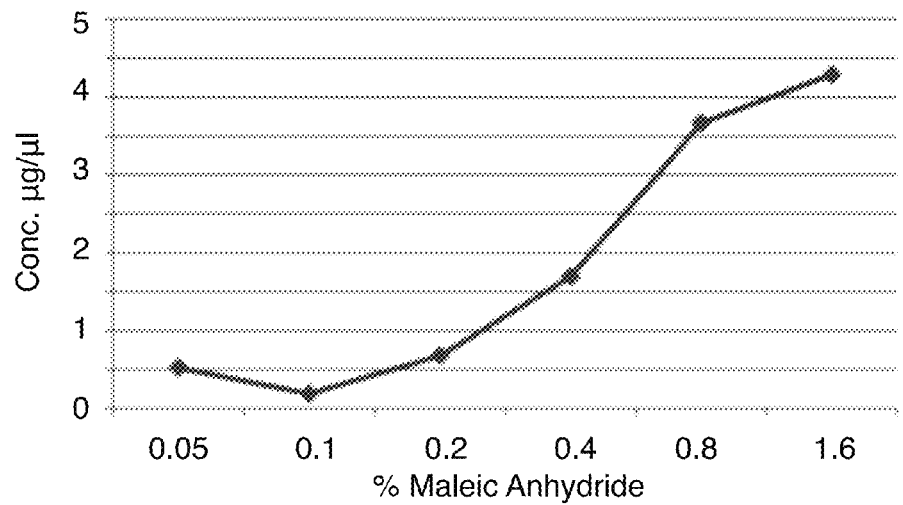
FIGS. 6A-6B illustrate the concentration of protein detected in fixed brain homogenates after heating in increasing concentrations of maleic acid (FIG. 6A) and the corresponding increase in GAPDH in a dot blot comparison (FIG. 6B).
Figure 6B:
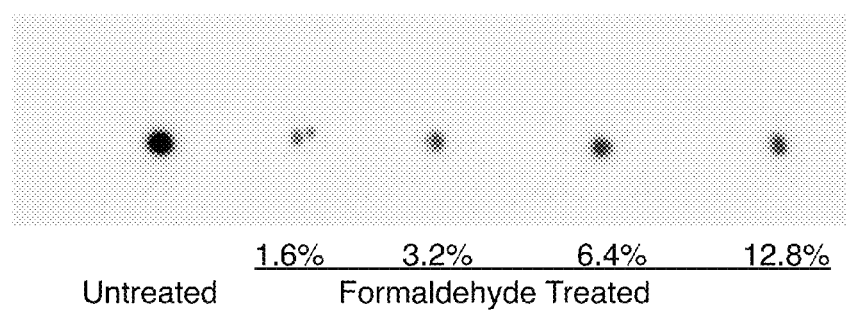

Due to its ability to crosslink and modify tissues, aldehyde-based fixation significantly impairs or prevents the use of fixed tissues in quantitative techniques to detect proteins, such as the Lowry and BCA assays, dot blotting or western blotting. This example demonstrates the utility of this invention in recovery of detectable protein. As shown in FIG. 6A, when formaldehyde-fixed protein homogenates from brain are heated in the presence of varying concentrations of maleic acid, the protein levels that are quantifiable by the BCA assay increases nearly 8-fold, indicating an increase in available free amino acids. However, unfixed protein that is similarly heated with maleic acid is readily detected by BCA and the concentration remains constant (data not shown). FIG. 6B is a dot blot comparison of detectable GAPDH protein, demonstrating that the use of these compounds leads to a significant and detectable increase of specific proteins. Formaldehyde treated tissues were treated with concentrations of maleic acid from 1.6% to 12.8% with heating at 95° C. for 30 minutes, demonstrating a parallel increase in the detection of GAPDH. In contrast, GAPDH was undetectable in untreated formaldehyde crosslinked tissue.

EXAMPLE 7

Antigen Retrieval in Adult Human Brain Vasculature

Paraformaldehyde fixed paraffin embedded tissue from adult human brain is treated with 2,3-dimethylmaleic acid as an antigen retrieval method as described. Blood vessels were detected using Collagen IV (FIG. 7).

EXAMPLE 8

Fluorescent Enhancement After Antigen Retrieval Process with the Addition of Triton Paraformaldehyde fixed paraffin embedded brain tissue is deparaffinized, heated to 70° C. for minutes for 30 minutes in solution, and then blood vessels are detected using Collagen IV (FIG. 8A-8B). Images are captured using 488 nM excitation. Addition of 0.5% Triton X-100 to a 5.0% ascorbic acid solution results in significant improvement in staining evenness and intensity (FIG. 8A) over the sample without Trition X-100 (FIG. 8B).

EXAMPLE 9

Autofluorescence Reduction by Treatment of Formulation for Antigen Retrieval

Figures 9A, 9B, 9C:
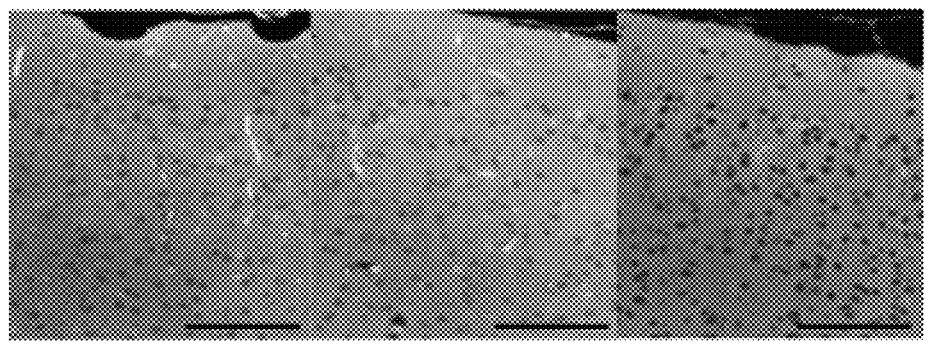
FIGS. 9A-9C show microscope images demonstrating the reduction of autofluorescence in heated tissues with 5% ascorbic acid (FIG. 9C) compared to heated tissue (FIG. 9B) and unheated tissue (FIG. 9A) without 5% ascorbic acid.

Paraformaldehyde fixed paraffin embedded brain tissue is deparaffinized, heated to 70° C. for minutes for 30 minutes in solution, and images are captured using 488 nM excitation (FIG. 9A-9C). Images are captured at same exposure and time. Compared with unheated tissue (FIG. 9A), tissue heated only in water (FIG. 9B) displayed enhanced tissue autofluorescence. Addition of 5% ascorbic acid under the same conditions dramatically reduces visible autofluorescence (FIG. 9C).

EXAMPLE 10

Increased Stability of Compounds with the Addition of Glutathione.

Figures 10A, 10B, 10C:
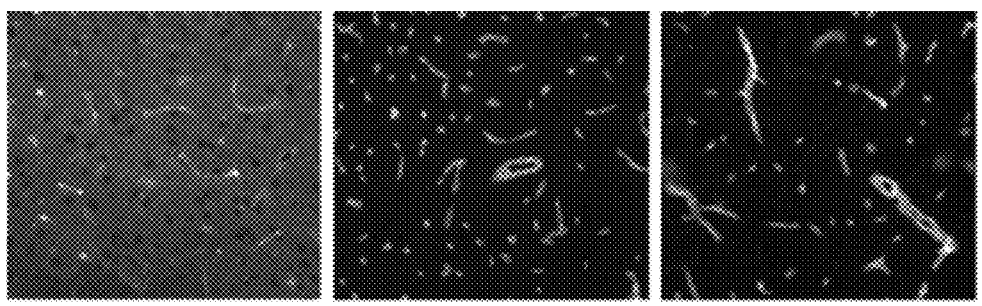
FIGS. 10A-10C show paraformaldehyde fixed paraffin embedded brain tissue is deparaffinized heated to 70° C. for 30 minutes with 2.8 mM glutathione (FIG. 10A), 5% ascorbic acid (FIG. 10B) and 2.8 mM glutathione+5% ascorbic acid (FIG. 10C) in solution.

Paraformaldehyde fixed paraffin embedded brain tissue is deparaffinized heated to 70° C. for 30 minutes in solution and images captured using 488 nM excitation with 20× magnification (FIG. 10A-10C). Images are captured at the same exposure and time at 20× magnification. Glutathione did not have an effect on tissue without the presence of ascorbic acid (FIG. 10A), compared to tissue heated in 5% ascorbic acid (negative control) (FIG. 10B). The addition of 2.8 mM glutathione to 5% ascorbic acid (FIG. 10C) increased stability of ascorbic acid while preserving staining.

EXAMPLE 11

Antigen Retrieval (Angiotensin I) Using Different Aldehyde Scavenging Compounds

Angiotensin I is treated with formalin at room temperature for 48 hours. Compounds including water at pH=3.5 (FIG. 11C), water at pH=5.5 (FIG. 11D), 5% imidazolidone (FIG. 11E), 5% citric acid (FIG. 11F), 5% guanidine (FIG. 11G), 5% maleic acid (FIG. 11H), Tris buffer at pH=3.5 (FIG. 11I), ascorbic acid (FIG. 11J), Hydroxylamine (FIG. 11K), cysteine (FIG. 11L) are respectively heated with the treated Angiotensin I at 95° C. for 45 minutes to test the ability of antigen retrieval for each compound. Mass-spectrometry is used to analyze the compositions of the Angiotensin I before and after treatment by each compound. Samples of Angiotensin I before (FIG. 11A) and after (FIG. 11B) formalin treatments are used as the controls for the experiment. The results of the test are shown in FIG. 11A-11L). Peaks at m/z 1296 represent unmodified Angiotensin I. Peaks at m/z 1308 represent Angiotensin I with 1 methylene unit. Peaks at m/z 1320 represent Angiotensin I with 2 methylene units. Peaks at m/z 1238 represent Angiotensin I with 1 methylene unit and 1 hydromethyl group. Peaks at m/z 1350 represent Angiotensin I with 2 methylene units and 1 hydromethyl group.

Figure 11A:
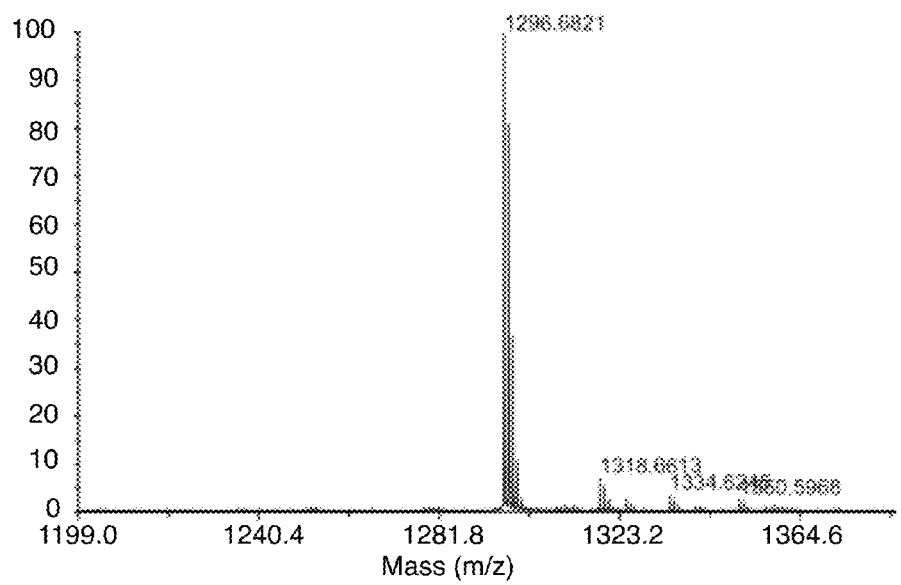
FIGS. 11A-11L show mass-spectrometry results for antigen retrieval of formalin treated Angiotensin I (FIGS. 11A-11B) using water at pH=3.5 (FIG. 11C), water at pH=5.5 (FIG. 11D), 5% imidazolidone (FIG. 11E), 5% citric acid (FIG. 11F), 5% guanidine (FIG. 11G), 5% maleic acid (FIG. 11H), 5% Tris buffer at pH=3.5 (FIG. 11I), 5% ascorbic acid (FIG. 11J), 5% hydroxylamine (FIG. 11K) and 5% cysteine (FIG. 11L).
Figure 11B:
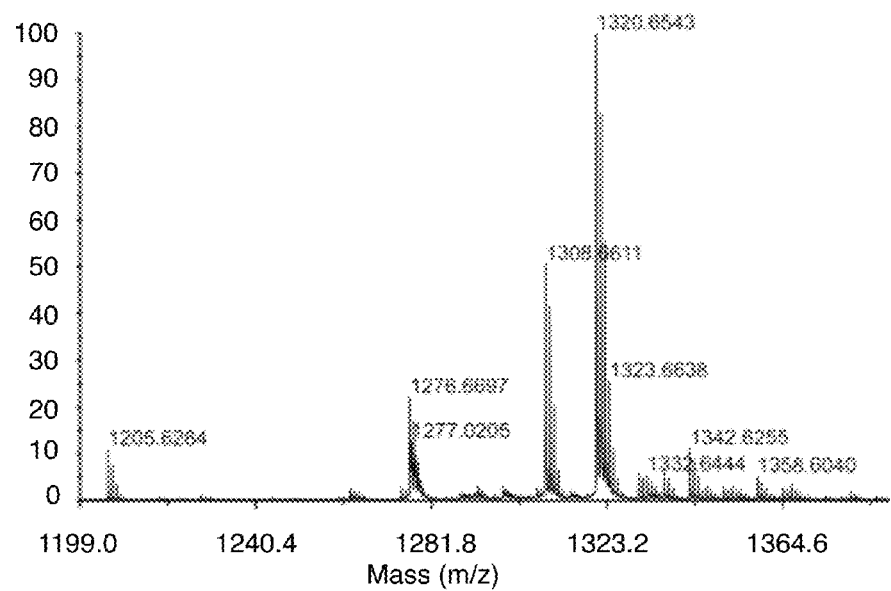
Figure 11C:
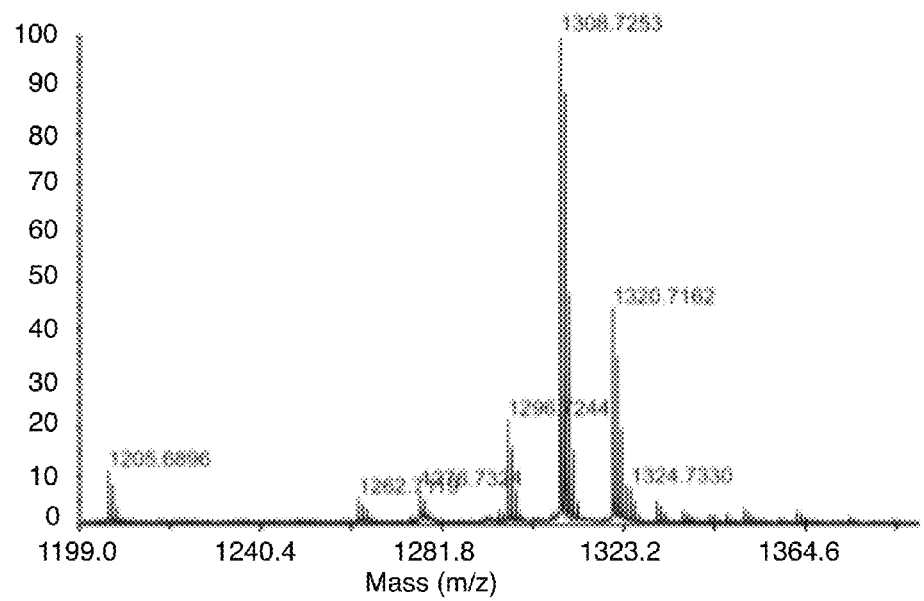
Figure 11D:
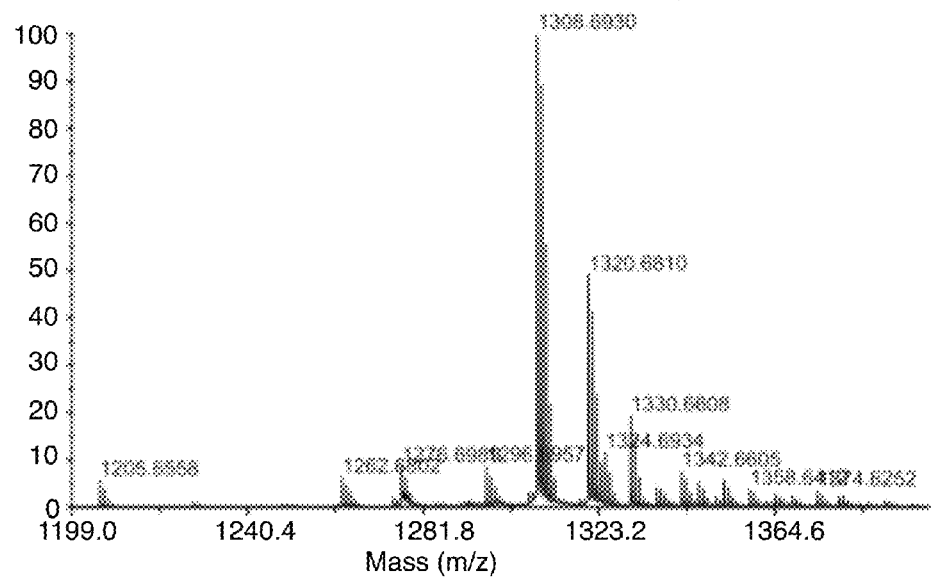
Figure 11E:
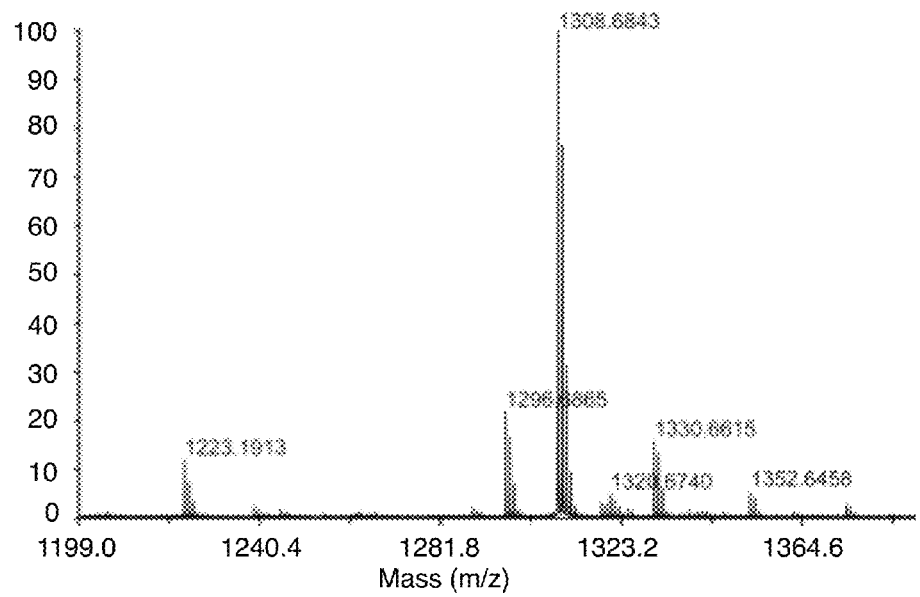
Figure 11F:
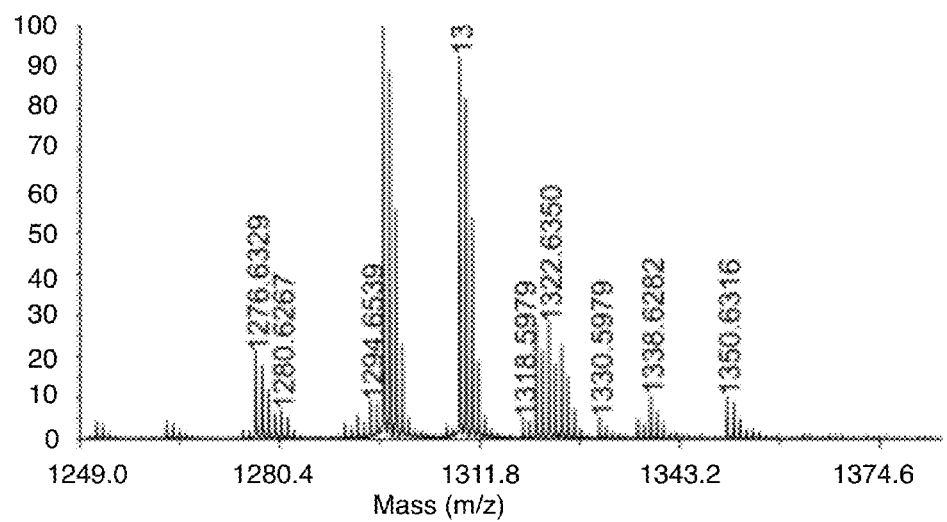
Figure 11G:
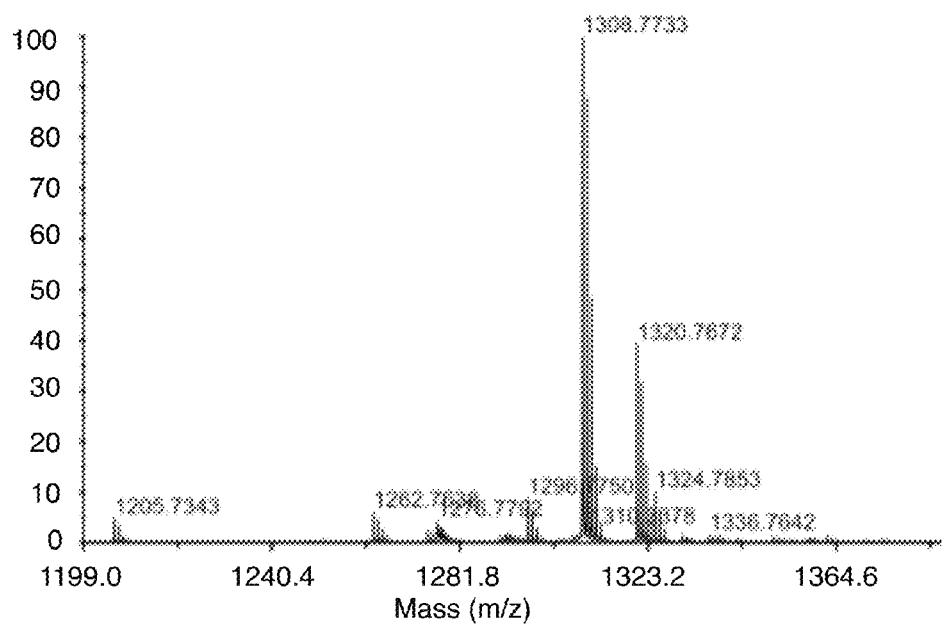
Figure 11H:
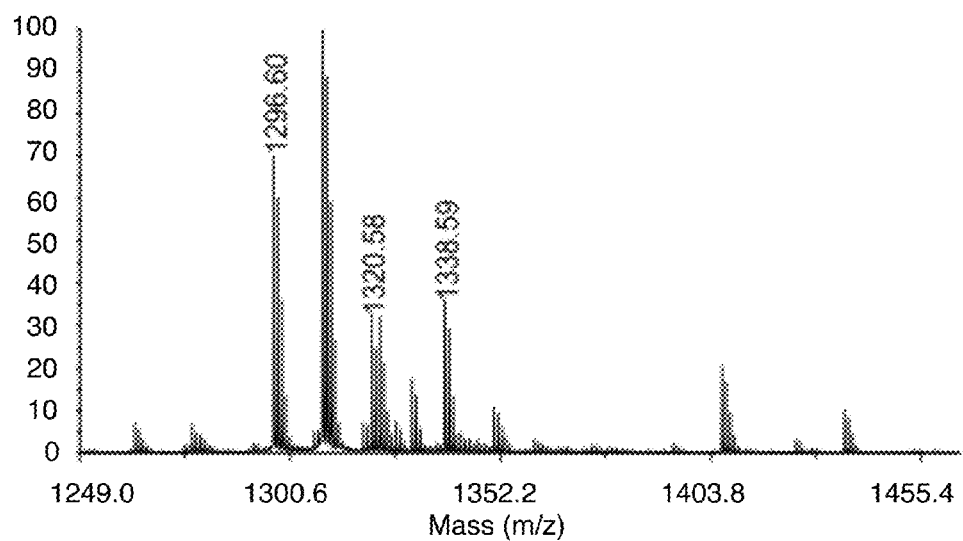
Figure 11I:
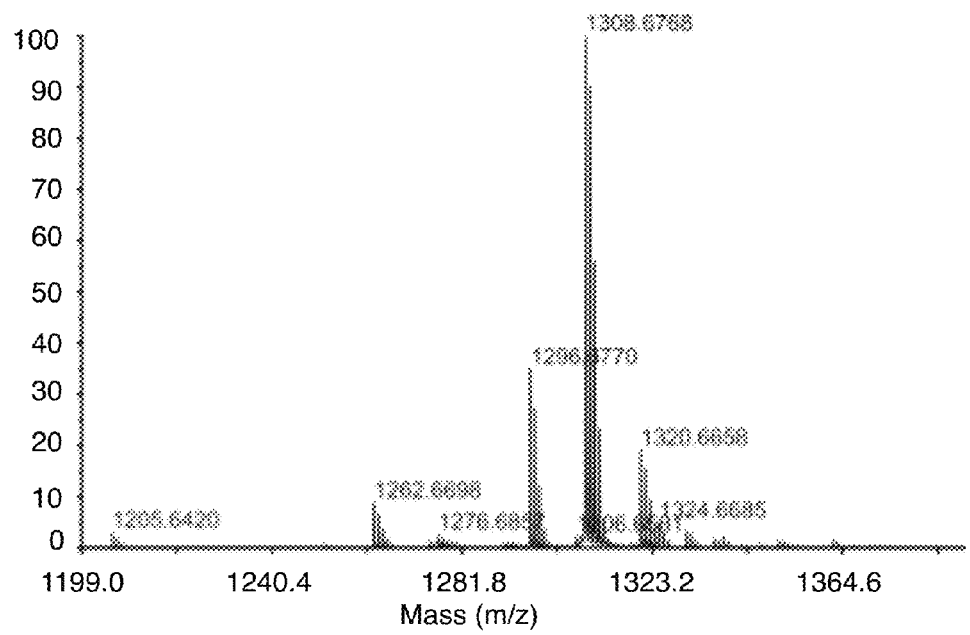
Figure 11J:
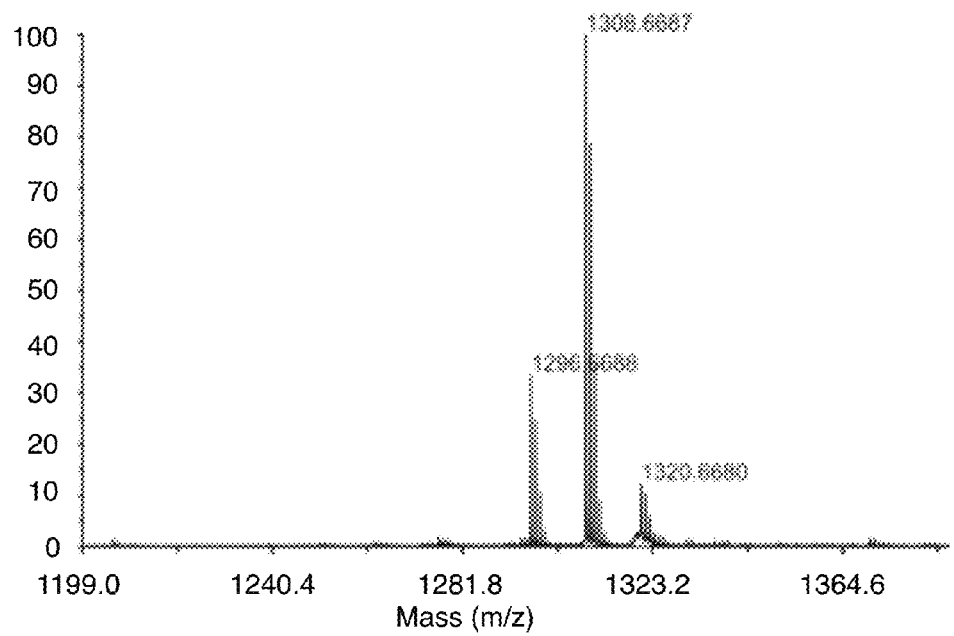
Figure 11K:
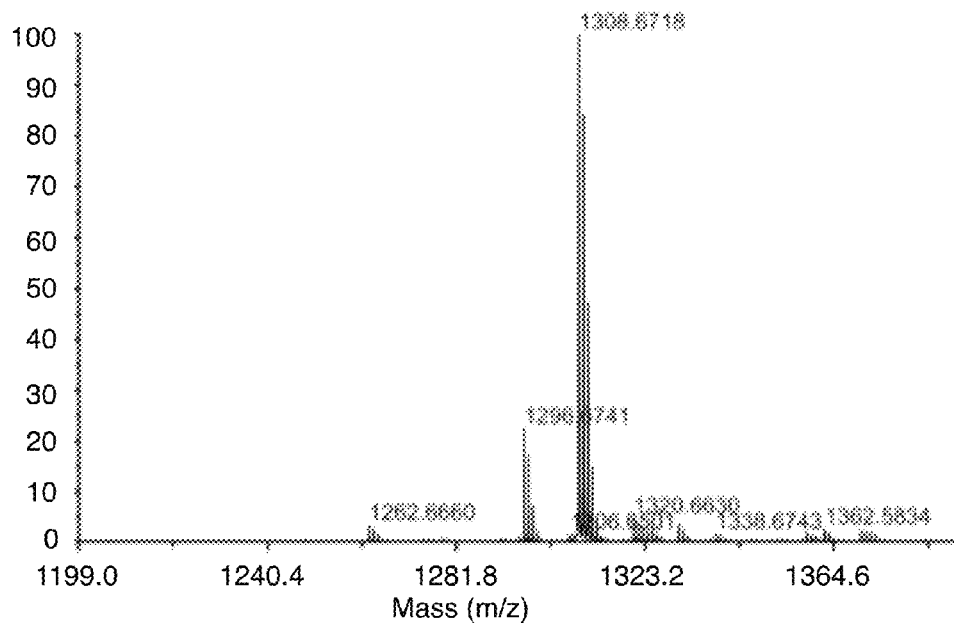
Figure 11L:
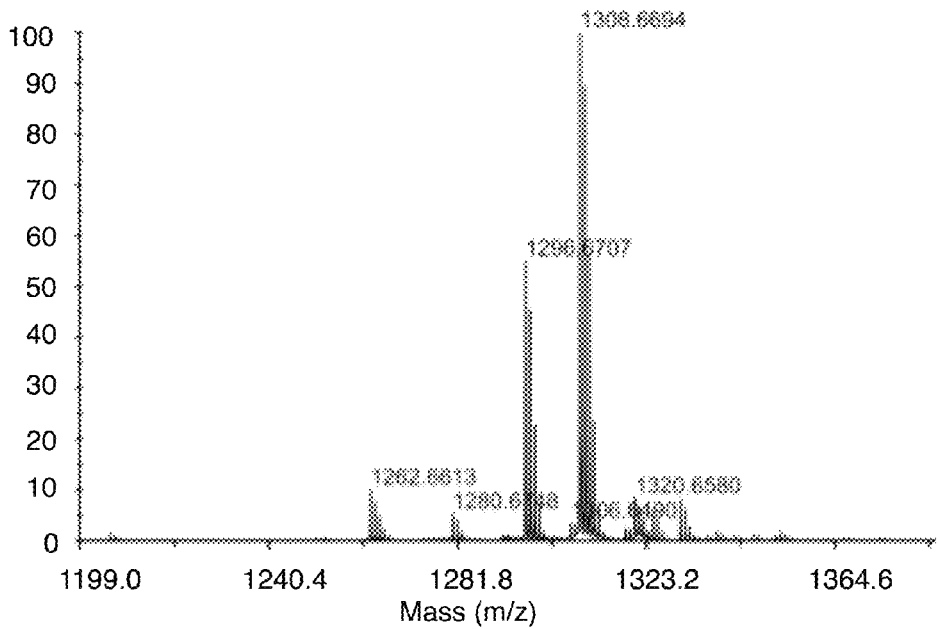

FIG. 11A-11B depicts the complete conversion of Angiotensin I to formalin-adducts. FIG. 11C-11D reveals that water at pH=3.5 has shown the ability of retrieval of formalin-adducts, but water at pH=5.5 exhibits almost no retrieval of formalin adducts. Comparisons of FIGS. 11B, 11D and 11G demonstrate that both 5% maleic acid and 5% imidazolidone are able to significantly reduce the amount of Angiotensin I with 2 methylene groups (m/z 1320), resulting in higher content of unmodified Angiotensin I (m/z 1296). Comparisons between FIG. 10B and FIG. 10F indicate that 5% citric acid (45 minutes, 95° C.) is able to significantly reduce the content of both Angiotensin I with 2 methylene units (m/z 1320) and Angiotensin with 1 methylene unit and 1 hydroxymethylene group (m/z 1338). FIG. 11G shows 5% guanidine exhibits minimal ability to retrieve Angiotensin I with 1 methylene unit and 1 hydroxymethylene group (m/z 1338), and does not exhibit any impact on the content of Angiotensin I with 2 methylene units (m/z 1320). Further, comparisons between FIG. 11B and FIGS. E and 11I-11L show 5% citric acid, 5% Tris buffer at pH=3.5, 5% ascorbic acid, 5% hydroxylamine and 5% cysteine all exhibits significant retrieval of formalin adducts.

EXAMPLE 12

Figure 12A:
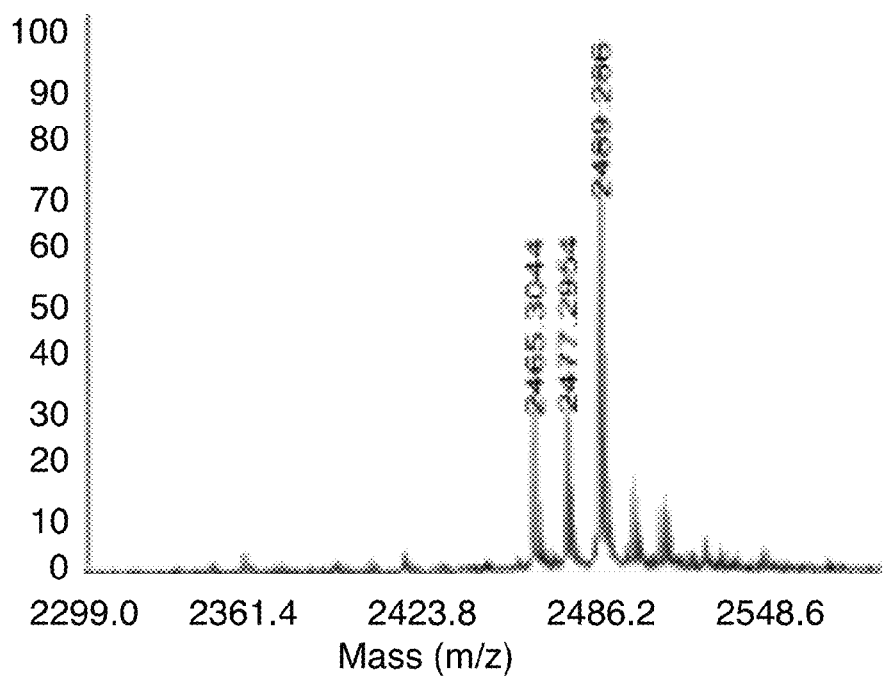
FIGS. 12A-12D show mass-spectrometry results for antigen retrieval of formalin treated ACTH (FIG. 12A) using 5% maleic acid (FIG. 12B), 5% ascorbic acid (FIG. 12C) and water (FIG. 12D). ACTH is treated with formalin at room temperature for 48 hours.
Figure 12B:
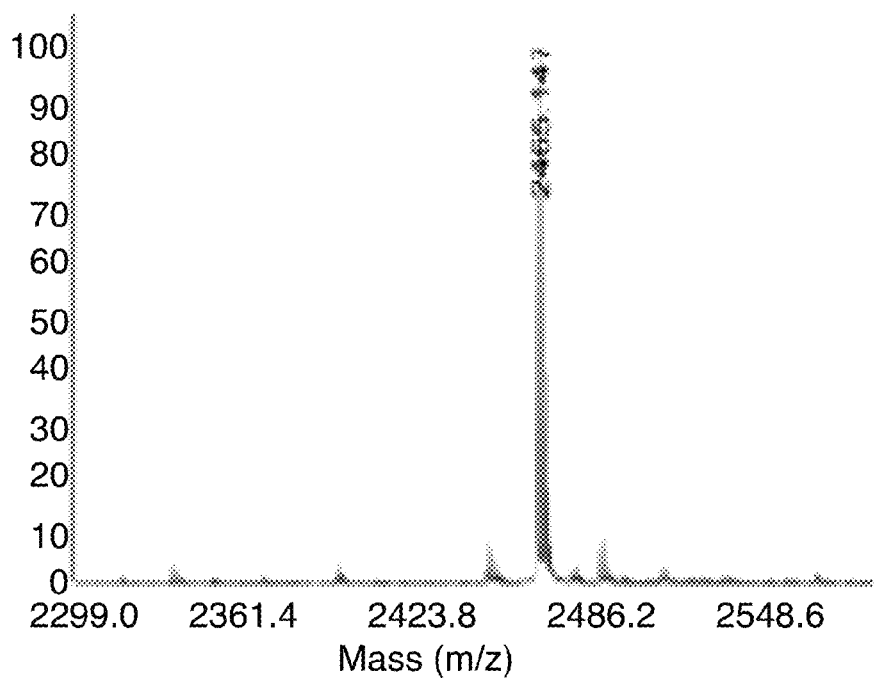
Figure 12C:
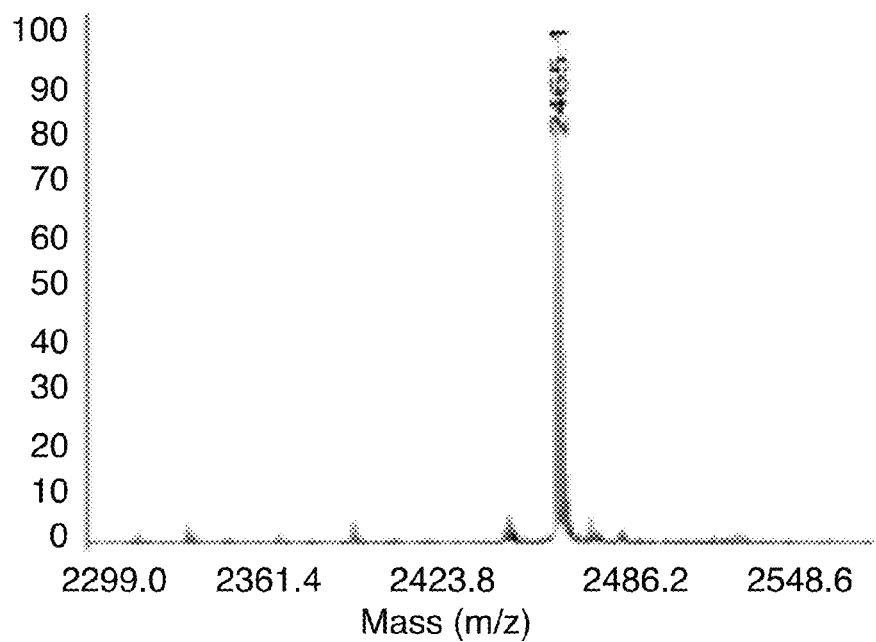
Figure 12D:
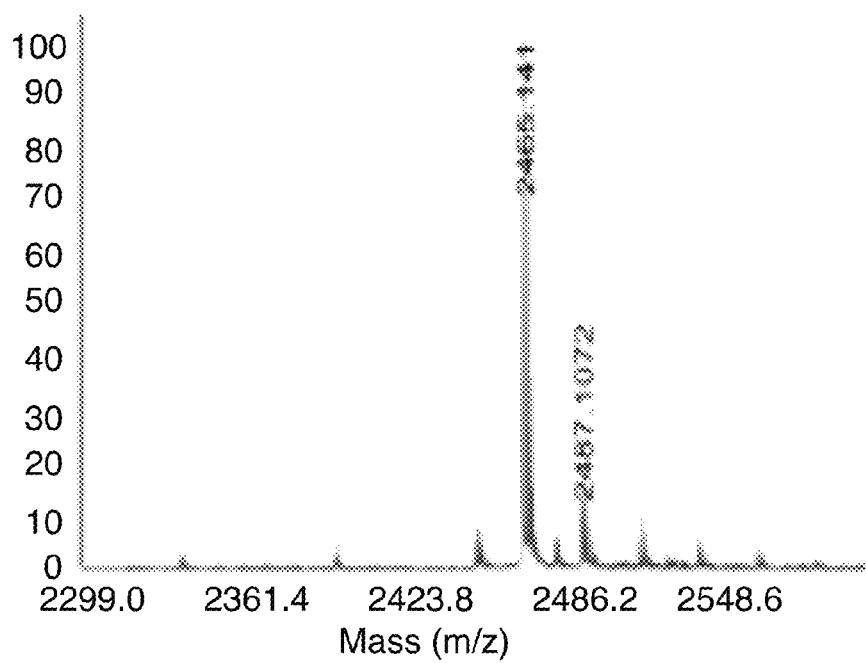

Antigen Retrieval (Adrenocorticotropic Hormone (ACTH)) by Formaldehyde Scavenging Agents ACTH (18-39) peptide is treated with formalin at room temperature for 48 hours (FIG. 12A). Then, 5% maleic acid (FIG. 12B), 5% ascorbic acid (FIG. 12C) and water at pH=3.5 (FIG. 12D) are used to treat the formalin treated ACTH peptide at 90° C. for 45 minutes respectively. The composition of the formalin treated ACTH after each treatment is analyzed using mass spectrometry. The results shown in FIGS. 12A-12D are used to investigate the ability of the agents to reverse formaldehyde adducts. FIG. 12A shows the composition of ACTH after formalin treatment, which results in high content of ACTH with 2 methylene units (m/z 2489) and ACTH with 1 methylene unit (m/z 2477). Only a small amount of ACTH with 3 methylene units is detected. Comparisons of FIGS. 12A, 12B, and 12C indicate that both 5% maleic acid and 5% ascorbic acid are able to convert almost all the modified ACTH (ACTH with 1, 2 or 3 methylene groups; m/z 2477, 2489 and 2501 respectively) into unmodified ACTH (m/z 2465) at 98° C. for 45 minutes.

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. Also, the terms in the claims have their plain, ordinary meaning unless otherwise explicitly and clearly defined by the patentee.

What is claimed is:

1. A method for retrieving antigens and detecting peptides and proteins in a fixed tissue, comprising the steps of:
   preparing a solution containing an aldehyde scavenging agent; and
   contacting a tissue fixed with an aldehyde-based cross-linking agent with said solution; wherein a reaction of the aldehyde scavenging agent with the aldehydes comprising the cross-linking agent retrieves the antigens and improves detection of the peptides and proteins in the fixed tissue.

2. The method of claim 1, wherein the aldehyde-based cross-linking agent is formaldehyde or glutaraldehyde.

3. The method of claim 1, wherein the concentration of the aldehyde scavenging agent in said solution is about 0.05% to about 30%.

4. The method of claim 3, wherein the pH of the solution is within a range specific for said aldehyde scavenging agents.

5. The method of claim 1, further comprising heating said solution to about 60° C. to about 125° C. to reach a reversible equilibrium between aldehyde and aldehyde adducts.

6. The method of claim 5, wherein said solution reduces autofluorescence in heated tissues.

7. The method of claim 1, further comprising the step of staining the tissue to detect the protein, peptide, an antigen or epitope comprising said protein, peptide, or antigen.

8. The method of claim 1, wherein the 2,3-substituted derivative is (E)-2 3-dideuteriobut-2-enedioic acid, (E)-2,3-dichlorobut-2-enedioic acid, Dichloromaleic acid, (Z)-2-hydroxy-3-methylbut-2-enedioic acid, (E)-2,3-difluorobut-2-enedioate, or 2-chloro-3-methylbut-2-enedioic acid.

9. The method of claim 1, wherein the solution further contains about 0.1% to about 5% of a nonionic surfactant which removes paraffin from a paraffin embedded sample and enhances fluorescence intensity of the detected proteins and peptides.

10. The method of claim 9, wherein the nonionic surfactant is Polyethylene glycol monohexadecyl ether, Cetostearyl alcohol, Cetyl alcohol, cocamide diethanolamine, cocamide monoethanolamine, Decyl glucoside, Octylphenoxypolyethoxyethanol, Polyethylene glycol monoisohexadecyl ether, Lauryl glucoside, Nonyl phenoxypolyethoxylethanol, 4-Nonylphenyl-polyethylene glycol, 1-(4-Nonylphenyl)-1,4,7,10,13,16,19,22,25-nonaoxaheptacosan-27-ol, nonoxynols, Monolaurin, Octaethylene glycol monododecyl ether, Oleyl alcohol, Polyethylene-polypropylene glycol, Polyglycerol polyricinoleate, Polysorbates, Sorbitan monostearate. Sorbitan tristearate; Stearyl alcohol; Polyethylene glycol p-(1,1,3,3-tetramethylbutyl)-phenyl ether; Polyoxyethylene (20) sorbitan monooleate. octyl-, decyl, dodecyl-glucopyranoside, -maltoside or deoxycholic acid.

11. The method of claim 1, wherein said solution further contains a stabilizing agent selected from a preservative, an antifungal agent, an antibacterial agent, a dye, a pigment, anionic detergents, metal salts, antioxidants or a combination thereof.

12. The method of claim 11, wherein said antioxidant is glutathione at a concentration of about 2 mM to about 400 mM.

* * * * *

UNITED STATES PATENT AND TRADEMARK OFFICE
CERTIFICATE OF CORRECTION

Page 1 of 1

PATENT NO.        : 9,506,928 B2
APPLICATION NO.   : 14/530142
DATED             : November 29, 2016
INVENTOR(S)       : Jason Eriksen et al.

It is certified that error appears in the above-identified patent and that said Letters Patent is hereby corrected as shown below:

In the Claims

Column 15, Line 38, after "aldehyde scavenging agent, the following should be added "that is maleic acid, fumaric acid or 2,3-disubstituted derivatives thereof, malic acid anhydride, 2,3-dimethylmaleic anhydride, ascorbic acid, imidazolidone, hydroxylamine, or cysteine";

Column 15, Line 43, "improves detection of" should be deleted and replaced with "detects";

Column 16, Line 16, "Dichloromaleic acid," should be deleted;

Column 16, Lines 36-38, the periods should be deleted.

Signed and Sealed this
Fourth Day of July, 2017

Joseph Matal
*Performing the Functions and Duties of the*
*Under Secretary of Commerce for Intellectual Property and*
*Director of the United States Patent and Trademark Office*